United States Patent [19]

Hemmes

[11] Patent Number: 4,558,589
[45] Date of Patent: Dec. 17, 1985

[54] ULTRASONIC COAGULATION MONITOR AND METHOD
[75] Inventor: Paul R. Hemmes, Elkhart, Ind.
[73] Assignee: Miles Laboratories, Inc., Elkhart, Ind.
[21] Appl. No.: 659,173
[22] Filed: Oct. 9, 1984
[51] Int. Cl.[4] .............................................. G01N 33/48
[52] U.S. Cl. ......................................... 73/64.1; 374/23
[58] Field of Search ...................... 73/64.1; 374/16, 23

[56] References Cited
U.S. PATENT DOCUMENTS 2,536,111  1/1951  Van Dyke ............................. 374/23
2,571,171  10/1951 Van Dyke ............................. 374/23

FOREIGN PATENT DOCUMENTS 2152805  4/1973  Fed. Rep. of Germany ....... 73/64.1

Primary Examiner—Stewart J. Levy
Assistant Examiner—Joseph W. Roskos
Attorney, Agent, or Firm—Roger N. Coe

[57] ABSTRACT

An ultrasonic coagulation monitor for measurement of prothrombin times and related coagulation times includes at least one piezoelectric crystal operated at a fixed frequency near its resonant frequency. A sample of material to be analyzed is placed in acoustic communication with the crystal. The voltage across the crystal is monitored in order to detect a voltage change, preferably a drop, that occurs upon coagulation of the sample. A timer is included that is turned off at a predetermined voltage drop corresponding to a particular stage of coagulation desired to be timed. In an alternative embodiment of the invention a second crystal is included and is mounted a predetermined distance from the first crystal to define a cavity therebetween. One crystal is driven by the frequency oscillator circuit and the material the coagulation of which is to be measured is placed in the cavity. A voltage sensing device senses the voltage across the second crystal and controls a timer as in the first embodiment.

29 Claims, 5 Drawing Figures

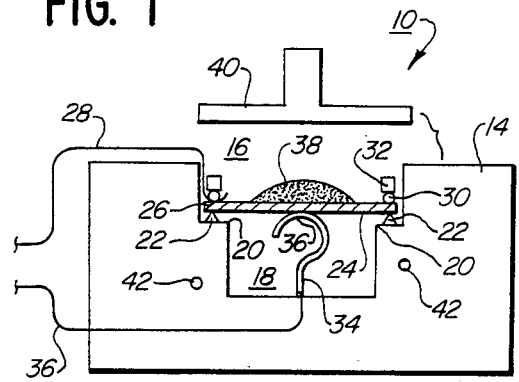
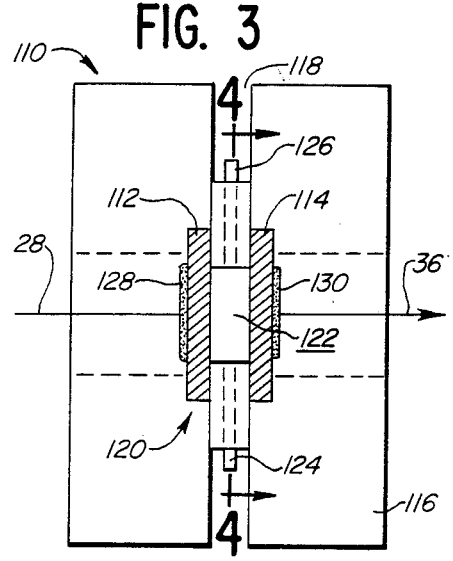
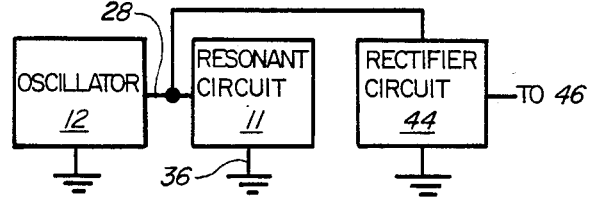
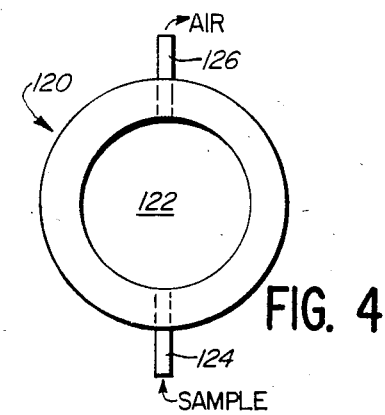
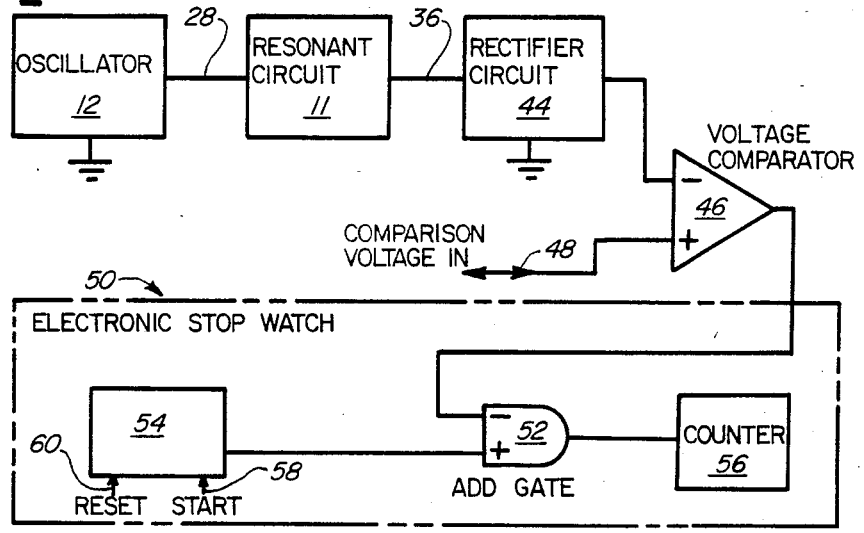

ULTRASONIC COAGULATION MONITOR AND METHOD

BACKGROUND OF THE INVENTION

A. Field of the Invention

The present invention relates to a new and improved method and apparatus for monitoring coagulation times. More particularly, the present invention is directed to an improved shear ultrasonic coagulation monitor for measuring prothrombin times and related coagulation times, and to an improved method for measuring the same using one or more piezoelectric crystals.

B. Description of the Background Art

Measurements of blood coagulation times are of clinical interest in evaluating patients with liver disease, and when clotting abnormalities are known to occur or are suspected. Patients on long term anticoagulant drugs require these measurements for the purpose of dosage adjustments. Generally, these measurements provide a rate-reaction record of clot formation which is characteristic of specific blood coagulation abnormalities. The instruments that perform these measurements allow recording of the entire clotting process in whole blood plasma and are suited to a wide range of clinical diagnostic applications and research studies.

Various tests and instruments for measuring clot formation are known. The simplest procedure for performing these tests is a manual test wherein a technician views a sample of blood and records the time required for a clot to form. Manual testing is simple but requires the total attention of the technician and quick reflexes, otherwise the test becomes error prone. Also, special lighting is required to permit the technician to see the clot formation.

In order to overcome the shortcomings of the manual procedure, several instruments utilizing mechanical or optical techniques to detect clot formation have been designed. One instrument, a clot timer manufactured by Mechrolab, uses a complex rotor that rotates or is stirred through the sample and measures resistance as coagulation occurs. A fibro-system coagulation timer by Becton, Dickinson & Co. drops a probe with fixed and movable electrodes into a cup containing blood, plasma or other material. Movable contacts in the probe cycle through the mixture. When a clot begins to form, movement of the contacts is resisted and a timer is stopped.

Instruments that combine mechanical and optical operating principles are also available. For example, some instruments employ magnetic stirrers to stir the sample and a light source and detector to detect a change in the motion of the stirrer indicative of clotting.

Seienco, Inc. of Morrison, Colo. manufactures an instrument identified as the Sonoclot coagulation analyzer. This instrument immerses a vibrating, disposable probe into a sample to measure the change in mechanical impedance imposed upon the probe by the changing visoelastic properties of the forming clot.

Each of these instruments is very expensive and bulky, thereby limiting their portability. Moreover, these instruments are extremely complex and difficult to maintain and service. In certain situations measurement of clotting times must be performed frequently and during the patient's normal workday. Consequently, it is beneficial to provide an inexpensive, small instrument to perform the desired measurements.

Research and theoretical analyses of the clotting process have also been conducted. Measurements of viscous properties in thin liquid layers close to a crystal surface have been discussed in papers by Th. Funck and F. Eggers entitled "Ultrasonic Relaxation Spectroscopy In Liquids" (appearing in Naturwissenschaften 69 1976) and "Clotting of Blood at a Gold Surface Probed by MHz Shear Quartz Resonator" (appearing in Naturwissenschaften 69 1982). These papers are devoted to the study of impedance of materials and examine clotting as a physical process. The procedures in these papers are not concerned with timing of the clotting process and employ complex instruments to perform the desired testing.

SUMMARY OF THE INVENTION

It is a principal object of the present invention to provide a new and improved method and apparatus for monitoring coagulation times that overcomes many of the disadvantages of the prior art systems.

Another object of the present invention is to provide a new and improved coagulation monitor.

Another object of the present invention is to provide a new and improved instrument for acoustically measuring prothrombin times and related coagulation times.

Another object of the present invention is to provide a new and improved coagulation monitor operating on a ultrasonic shear principle.

A further object of the present invention is to provide a new and improved method for measuring prothrombin times and related coagulation times.

Still another object of the present invention is to provide a new and improved coagulation monitor using a piezoelectric crystal in a fixed frequency circuit.

Yet another object of the present invention is to provide a small, inexpensive coagulation monitor that is substantially automatic, thereby eliminating the need for constant attention by an attendant.

In accordance with the present invention, an instrument is provided for measuring prothrombin times and related coagulation times operating on the principle of shear ultrasonics. The instrument includes, in a first embodiment, a piezoelectric crystal that is connected in a fixed frequency oscillator circuit. A sample to be analyzed is placed on the piezoelectric crystal. An impedance analyzer is used to measure the resonant voltage across the crystal, and to turn off a timer upon the reduction in the amplitude of resonant voltage to a predetermined level indicative of clot formation.

In a second embodiment a second crystal is positioned a predetermined distance from a first crystal to define a cavity. The first crystal is driven by the previously mentioned circuit. The change in resonant voltage across the second crystal is measured as a sample in the cavity coagulates. As in the first embodiment, a timer is turned off upon the resonant voltage reaching a predetermined level.

A method for measuring prothrombin times and related coagulation times is also disclosed. The method includes the steps of placing a sample of the material to be measured onto a piezoelectric crystal and driving the crystal at a fixed frequency. The resonant voltage is measured and a timer is turned off once the voltage drops to a predetermined level.

BRIEF DESCRIPTION OF THE DRAWINGS

Other and further objects, advantages and features of the invention will be apparent to those skilled in the art from the following detailed description thereof, taken in conjunction with the accompanying drawings in which:

FIG. 1 is a schematic illustration of a shear ultrasonic coagulation monitor constructed in accordance with the principles of the present invention;

FIG. 2 is a block diagram of a circuit including the monitor illustrated in FIG. 1 and a timer for timing prothrombin and related coagulation times, the monitor includes a crystal in series with an oscillator;

FIG. 2a is a block diagram illustrating the monitor in parallel with an oscillator;

FIG. 3 is a schematic illustration of a resonant cavity for monitoring coagulation; and FIG. 4 is a view taken generally along line 4—4 of FIG. 3.

DETAILED DESCRIPTION OF PREFERRED EMBODIMENTS

The present invention is based on the principle that whole blood is a relatively low sound absorber, and as whole blood coagulates, large changes in acoustic properties occur. By detecting these changes, the time at which coagulation occurs can be readily detected. Such changes can be detected by placing a sample of blood to be evaluated on a piezoelectric resonator such as a quartz crystal or ceramic resonator, or similar device, and by noting the changes in the resonant characteristics of the resonator that occur upon coagulation. This can be accomplished by driving the resonator at or near its resonant frequency by a suitable oscillator or signal generator and measuring the voltage appearing across the resonator, or by measuring the impedance of the resonator either directly or indirectly. As long as the blood sample remains liquid, it will have very little effect on the Q, or quality factor, of the resonant circuit formed by the resonator and blood sample, where Q equals the resonant frequency divided by the width of the resonance curve of half height. Consequently, the Q of the circuit will be determined primarily by the resonator, which is a high-Q device. Upon coagulation, the coagulated blood will damp the oscillatory motion of the crystal, thereby lowering its Q. The resonant frequency of the crystal and the coagulated blood combination will generally also be lower. Thus, by measuring the impedance of the crystal circuit, the voltage across the crystal or the resonant frequency, the occurrence of coagulation can be readily detected. Upon detection of such a change, a timer that was started at the beginning of the test is automatically shut off to provide an indication of the clotting time.

For a more detailed description of the present invention reference is made to the drawings and specifically to FIG. 1. Referring to FIG. 1, there is illustrated a sample receiving analyzer portion of the coagulation monitor generally designated by the reference numeral 10. The analyzer 10 is intended to be reusable and cleanable. No particular configuration of the analyzer 10 is preferred but in the embodiment illustrated the analyzer 10 includes a housing 14 of a generally rectangular configuration. The housing 14 is fabricated from a washable material such as plexiglas. The housing 14 includes first and a second cavities 16 and 18 that are open to each other.

A shelf or lip 20 is defined between the cavities 16 and 18 and supports 22 are positioned on the shelf 20. The supports 22 can be, for example, three pinpoint supports, edge supports or sharp hard points made of Teflon, preferably arranged not to dampen the movement of a piezoelectric crystal 24 placed on supports 22. The crystal 24 is preferably a quartz crystal such as an AT or Y cut crystal. Preferably an AT cut crystal operating in a shear mode is used wherein the surfaces of the crystal vibrate in a direction parallel to the surface, although other vibrational modes, and other materials such as lithium niobate can be used. The crystal 24 can be obtained from Valpey-Fisher of Hopkinton, Mass. and other manufacturers. The crystal 24 can be of any configuration although circular is preferred.

A physical constraint of a shear mode crystal such as crystal 24 is thickness. Thickness of crystal 24 is related to the wavelength of sound in crystal 24 at its fundamental frequency. The thinner the crystal, the higher its frequency. It has been determined that a crystal 24 with a fundamental frequency of 20 mega hertz (MHz) is difficult to handle. Accordingly, the frequency range of the crystal 24 in compliance with the physical constraint of thickness can be in the 5–20 MHz range, and a preferred range is 10–15 MHz.

The surfaces of the crystal 24 include evaporated electrodes and are plated with gold or similar electrically conductive chemically stable material to permit electrical contact to be made to the crystal. The outer edge 26 is not plated to prevent shorting between the surfaces. An electrical lead 28 is electrically connected to the plated portion of crystal 24. The lead 28 and crystal 24 are held in position on the supports 22 by a rubber 0-ring 30 and a split ring 32. A spring loaded contact 34 is mounted in cavity 18 with an upper end 36 engaging the lower plated surface of crystal 24. Contact 34 does not dampen movement of the crystal 24 but provides electrical contact between crystal 24 and electrical lead or wire 36.

To time coagulation, a sample 38 of plasma or similar material is pipetted onto the upper surface of the crystal 24. If desired, a cover 40 can then be placed over cavity 16 to maintain heat from the sample within cavity 16. Since the temperature of the human body is 98.6° F. or 37° C., the sample 38 may be at this temperature prior to placement on the crystal 24, and cover 40 will reduce heat loss and maintain the temperature of sample 38 at 37° C. The cover 40 is not absolutely necessary since timing of coagulation requires a short span of time and loss of heat from sample 38 will be minimal. In addition, housing 14 may be heated by a pair of thermostatically controlled heating members 42 if desired.

The clotting process involves several stages, and reagents such as American Dade reagents distributed by American Hospital Supply Corporation can be mixed with sample 38 to allow study of the various stages. These stages are studied with the assistance of the analyzer 10 by employing the principle that the ability of the crystal 24 to vibrate is proportional to the square root of the viscosity of the sample 38. Using this principle the following procedure or method is performed by the analyzer 10. Crystal 24 is energized by applying to the crystal an oscillatory signal at or near its resonant frequency. If the crystal 24 is a shear mode crystal, as previously discussed, the surface of the crystal will vibrate in a back and forth direction parallel to the surface beneath the sample 38. As long as the sample 38 remains liquid, it will have very little affect on the vibration of the crystal 24 since a liquid can sustain little or no shear force. However, once sample 38 begins to coagulate, its viscosity will increase as will its ability to sustain a shear force. This will dampen the impedance and the resonant frequency of the combination of crystal 24 and sample 38. The loading will reach its maximum when sample 38 coagulates fully. The degree of coagulation is reflected in the impedance between the leads 28 and 36.

The impedance between the leads 28 and 36 can be measured in a variety of ways. One suitable way is to use an impedance analyzer, such as, for example, the impedance analyzer manufactured by Hewlett-Packard Incorporated of Palo Alto, Calif. The use of an impedance analyzer to measure impedance has the advantage that the crystal can be operated either at series resonance, parallel resonance or in the region between series and parallel resonance since an impedance change in this region is easy to detect. However, an impedance analyzer is relatively expensive and requires a considerable amount of skill to operate.

Another way in which the impedance change can be detected is to operate the crystal either at series resonance or in parallel resonance with a fixed-frequency oscillator. If the crystal is operated in its parallel resonance mode, the voltage across the leads 28 and 36 will be at its maximum value at parallel resonance. As the sample 38 coagulates, resonant frequency of the system will drop as will the Q of the circuit. Both factors will cause a drop in the voltage across the leads 28 and 36 that will be readily detectable.

The crystal 24 can also be driven at a frequency close to its series resonance frequency. At the series resonant frequency, the impedance of the crystal is at its lowest, and when the sample 38 coagulates, the impedance between the leads 28 and 36 will rise. The rise in impedance can also be used to detect the coagulation of the sample 38, as is illustrated in FIG. 2.

Referring to FIG. 2, the analyzer 10 is generally defined in block diagram form as a resonant circuit 11. The resonant circuit 11 is connected by one of the leads 28 and 36, for example, the lead 28, to an oscillator 12 that is oscillating at or near the series resonant frequency of the resonant circuit 11. The other one of the leads 28 and 36, for example, the lead 36, is connected to a rectifier circuit 44. Thus, when the resonant circuit 11 is in series resonance, its impedance is at a minimum and the maximum signal is applied to the rectifier circuit 44. The signal from the resonant circuit 11 is rectified by the rectifier circuit 44 to provide a D.C. voltage to a voltage comparator 46. The amplitude of the rectified signals from the rectifier circuit 44 is also at a maximum when the resonant circuit 11 is in series resonance.

The voltage comparator 46 compares the signal from the rectifier circuit 44 with a comparison voltage 48 defining a particular level of coagulation and sends a signal to an electronic stopwatch 50 to stop the stopwatch 50 when that level has been reached. More specifically, the signal from the comparator is provided to an AND gate 52 to prevent clock pulses from a clock circuit 54 from being applied to a counter 56. Thus, the accumulated count in the counter 56 when coagulation of sample 38 occurs is a measure of the coagulation time. The elapsed time can be recorded and evaluated. The electronic stopwatch 50 includes a start switch 58 and a reset switch 60 allowing manual starting of stopwatch 50 when the sample 38 is placed on the crystal 24 and automatic shut off.

Alternatively, resonant circuit 11 can be operated at parallel resonance so that the impedance of the resonant circuit 11 is at its maximum, thereby resulting in a minimum signal being applied to the rectifier circuit 44 prior to coagulation. As coagulation occurs, the frequency shift and Q reduction will cause the impedance of the resonant circuit 11 to drop, thereby decreasing the impedance of the resonant circuit 11 and increasing the power of the signal applied to the rectifier 44. This will increase the amplitude of the voltage applied to the voltage comparator 46 when coagulation occurs. This voltage increase can be used to stop the stopwatch 50 in much the same manner as was done by the voltage decrease in the previously discussed embodiment; however, a change in the stopwatch control circuitry, sucn as, for example, a change in the input polarities to the voltage comparator 46 must be made.

In yet another embodiment, the resonant circuit 11 can be connected in parallel with the oscillator 12 and the rectifier circuit 44 (FIG. 2a). In such a configuration, the resonant circuit 11 can be preferably operated in a parallel resonant mode with the voltage across the circuit 11 being monitored by the recitifier circuit 44. In such a configuration, a predetermined voltage drop would be used to determine the coagulation point. Alternatively, the resonant circuit 11 can be operated in a series resonant mode, and the voltage thereacross monitored with an increase in voltage being used to stop the stopwatch 50 to indicate clotting.

An alternative analyzer is provided by a resonant cavity 110 illustrated in FIG. 3. The resonant cavity 110 is defined by a pair of crystals 112 and 114 mounted vertically in a housing 116. The housing 116 can be metal or plexiglas. A cavity 118 is defined between crystals 112 and 114 and a sample holder 120 is positioned in cavity 118. As illustrated in FIG. 4, the sample holder 120 is circular defining a central cavity 122. Communication with the cavity 122 is provided by a pair of tubes 124 and 126. Sample material such as the sample 38 is introduced into cavity 122 through the lower tube 124. Filling cavity 122 through lower tube 124 forces air out of cavity 122 through tube 126 thereby minimizing bubbles in the sample 38.

Wire 28 is coupled to crystal 112 by securing material 128, which can be gold plating. When the analyzer 110 is used as the resonant circuit 11 of FIG. 2, crystal 112 is connected by wire 28 to oscillator 12 and is the driven crystal. Shear waves in crystal 112 are not transmitted through sample 38 until coagulation occurs. As coagulation occurs, shear waves are sensed by crystal 114, thus causing the crystal 114 to generate a voltage that is communicated to the rectifier circuit by wire 36 which is connected to crystal 114 by securing material 130. A pair of wires (not shown) are connected to the inner surfaces of the crystals 112 and 114 to ground or a source of common potential to complete the circuit. The electronic stopwatch 50 is turned off as previously described.

Either analyzer 10 or 110 provides a small, inexpensive instrument to measure coagulation and prothrombin times. The analyzers 10 and 110 use an ultrasonic technique that insures accuracy and requires little maintenance since there are few moving parts.

Obviously, many modifications and variations of the invention as set forth can be made without departing from the spirit and scope thereof and therefore only such limitations should be imposed as are indicated by the appended claims.

What is claimed is:

1. A ultrasonic coagulation monitor, comprising:
a housing,
at least one piezoelectric crystal mounted in said housing,
means for driving said crystal at a fixed frequency,
a timer, and
means for measuring resonant voltage in a circuit defined by said crystal and said driving means and for turning off said timer upon said voltage dropping to a predetermined level.

2. The ultrasonic coagulation monitor set forth in claim 1 wherein said piezoelectric crystal is operated in a shear mode of resonance.

3. The ultrasonic coagulation monitor set forth in claim 1 wherein said piezoelectric crystal comprises an AT cut quartz crystal.

4. The ultrasonic coagulation monitor set forth in claim 1 wherein said crystal is a lithium niobate crystal.

5. The ultrasonic coagulation monitor set forth in claim 1 wherein said crystal is circular in configuration.

6. The ultrasonic coagulation monitor set forth in claim 1 wherein the fundamental frequency of said crystal is in the range of 5-20 MHz.

7. The ultrasonic coagulation monitor set forth in claim 1 further comprising a second crystal mounted in said housing spaced a predetermined distance from said first crystal to define a resonant cavity between said first and second crystals.

8. The ultrasonic coagulation monitor set forth in claim 1 further comprising a cover for said housing.

9. The ultrasonic coagulation monitor set forth in claim 1 further comprising means for maintaining the temperature in said housing at approximately 37° C.

10. The ultrasonic coagulation monitor set forth in claim 1 wherein said housing includes means for supporting said crystal including pin points.

11. The ultrasonic coagulation monitor set forth in claim 1 wherein said housing includes means for supporting said crystal including a sharp edge.

12. The ultrasonic coagulation monitor set forth in claim 1 further comprising supports in said housing supporting said crystal wherein said supports are Teflon coated.

13. The ultrasonic monitor set forth in claim 1 wherein said resonant voltage measuring means includes a voltage comparator.

14. A device for measuring coagulation times, comprising:
at least one piezoelectric crystal,
means for supporting each said crystal to allow each said crystal to oscillate in the plane of each said crystal,
means for defining with said crystal a fixed frequency oscillator circuit,
a timer, and
means for measuring a change in resonance voltage in said oscillator circuit and for turning off said timer upon said resonance voltage changing to a predetermined value.

15. The device claimed in claim 14 further comprising a housing, each said at least one crystal being mounted in said housing.

16. The device claimed in claim 14 further comprising means for maintaining the temperature in said housing at approximately 37° C.

17. The device claimed in claim 14 wherein said oscillator circuit includes a fixed frequency generator with a resonant frequency of 5-20 MHz.

18. The device claimed in claim 14 wherein each said at least one crystal is a quartz crystal cut along the Y axis and each is of a fundamental frequency of 5-20 MHz.

19. The device claimed in claim 14 wherein said measuring means includes an impedance analyzer.

20. The device claimed in claim 14 wherein said supporting means comprises pin points.

21. The device claimed in claim 14 further comprising a second crystal supported by said supporting means a predetermined distance from said at least one crystal to define a cavity therebetween.

22. The device claimed in claim 14 wherein each said crystal includes evaporated electrodes.

23. An ultrasonic coagulation monitor, comprising:
a pair of piezoelectric crystals;
means for mounting said crystals a predetermined distance apart to define a cavity therebetween;
means for energizing at least one of said crystals with a fixed frequency oscillator circuit;
a timer; and
means for sensing a voltage at the other of said piezoelectric crystals and turning off said timer upon said voltage reaching a predetermined amplitude.

24. The monitor set forth in claim 23 wnerein said mounting means includes a housing and means for heating said cavity to 37° C.

25. The monitor set forth in claim 23 wherein said voltage sensing means includes a voltage comparator.

26. The monitor set forth in claim 23 wherein said crystals comprise AT cut quartz crystals.

27. A method of monitoring coagulation times of material comprising the steps of:
placing material, the coagulation time of which is to be measured, in sound absorbing relationship with at least one piezoelectric crystal;
driving said at least one crystal at a fixed frequency using a fixed frequency oscillator circuit;
detecting a predetermined voltage change in said oscillator circuit; and
determining the time required for the voltage change to occur.

28. The method set forth in claim 27 further comprising the step of maintaining the temperature of said material at 37° C.

29. The method set forth in claim 27 further comprising the step of driving said at least one crystal at 5-20 MHz.

* * * * *